United States Patent
Bob (10) Patent No.: US 12,042,122 B2
(45) Date of Patent: Jul. 23, 2024

(54) ENDOSCOPE HEAD HAVING A PIVOTABLE CAMERA AND WORKING CHANNEL UNIT

(71) Applicant: Konstantin Bob, Weinheim (DE)

(72) Inventor: Konstantin Bob, Weinheim (DE)

( * ) Notice: Subject to any disclaimer, the term of this patent is extended or adjusted under 35 U.S.C. 154(b) by 133 days.

(21) Appl. No.: 16/604,741

(22) PCT Filed: Apr. 11, 2018

(86) PCT No.: PCT/EP2018/059265
§ 371 (c)(1),
(2) Date: Oct. 11, 2019

(87) PCT Pub. No.: WO2018/189230
PCT Pub. Date: Oct. 18, 2018

(65) Prior Publication Data
US 2020/0100656 A1    Apr. 2, 2020

(30) Foreign Application Priority Data

Apr. 12, 2017   (DE) .......................... 102017107978.5

(51) Int. Cl.
*A61B 1/00*    (2006.01)
*A61B 1/005*   (2006.01)
(Continued)

(52) U.S. Cl.
CPC ...... *A61B 1/00098* (2013.01); *A61B 1/00096* (2013.01); *A61B 1/00101* (2013.01);
(Continued)

(58) Field of Classification Search
CPC .............. A61B 1/0008; A61B 1/00087; A61B 1/00089; A61B 1/00098; A61B 1/00101;
(Continued)

(56) References Cited

U.S. PATENT DOCUMENTS 5,413,107 A * 5/1995 Oakley ............. A61M 25/0136
                                                600/463
5,456,258 A * 10/1995 Kondo ................... A61B 8/445
                                                600/463
(Continued)

FOREIGN PATENT DOCUMENTS

DE            10209986 A1    10/2003
DE       102010034380 A1     2/2012
(Continued)

OTHER PUBLICATIONS

German Search Report for German Application No. 10 2017 107 978.5, with English translation, dated Nov. 29, 2017, 20 pages.
(Continued)

*Primary Examiner* — Ryan N Henderson
*Assistant Examiner* — Pamela F Wu
(74) *Attorney, Agent, or Firm* — Buchanan Ingersoll & Rooney PC (57) ABSTRACT

An endoscope head or endoscope head attachment for retrofitting a generally known endoscope having an existing internal endoscope head has at least one individual optical unit for image transmission; a lighting source; and a working channel for guiding tools and/or for media to flow through. In addition, the endoscope head or attachment has an internal pivoting device which is designed to pivot at least one section of the endoscope head or attachment from a prograde orientation into a lateral or a retrograde orientation. The optical unit and the working channel of the endoscope head or attachment are coupled directly or indirectly to the pivoting device, so that they can be pivoted together with the latter.

20 Claims, 4 Drawing Sheets

(51) Int. Cl.
*A61B 1/018* (2006.01)
*A61B 1/05* (2006.01)
*A61B 1/273* (2006.01)
*A61B 1/31* (2006.01)

(52) U.S. Cl.
CPC ...... *A61B 1/00137* (2013.01); *A61B 1/00177* (2013.01); *A61B 1/0055* (2013.01); *A61B 1/018* (2013.01); *A61B 1/05* (2013.01); *A61B 1/2736* (2013.01); *A61B 1/31* (2013.01)

(58) Field of Classification Search
CPC .............. A61B 1/00137; A61B 1/0014; A61B 1/00174; A61B 1/00177; A61B 1/00179; A61B 1/00183; A61B 1/018; A61B 1/05; A61B 1/053; A61B 1/00131; A61B 1/0055; A61B 1/0051; A61B 1/012; A61B 1/005; A61B 1/0125; A61B 1/31
USPC .................................. 600/107, 173–175, 129
See application file for complete search history.

(56) References Cited

U.S. PATENT DOCUMENTS

| | | |
|---|---|---|
| 2002/0099267 A1 | 7/2002 | Wendlandt et al. |
| 2003/0181785 A1 | 9/2003 | Viebach et al. |
| 2005/0234526 A1 | 10/2005 | Gilhuly et al. |
| 2009/0231419 A1 | 9/2009 | Bayer |
| 2010/0056861 A1* | 3/2010 | Spivey ............. A61B 17/00234 600/106 |
| 2010/0228086 A1 | 9/2010 | Ohki et al. |
| 2011/0028790 A1 | 2/2011 | Farr et al. |
| 2012/0041264 A1 | 2/2012 | Blase |
| 2012/0041266 A1* | 2/2012 | Buehs ................ A61B 1/0057 600/142 |
| 2012/0123212 A1* | 5/2012 | Dahmen ............ A61B 1/00167 600/178 |
| 2014/0107417 A1 | 4/2014 | Mckinley et al. |
| 2015/0238068 A1 | 8/2015 | Rose et al. |
| 2017/0127915 A1 | 5/2017 | Viebach et al. |
| 2017/0231474 A1* | 8/2017 | Saadat ............... A61B 1/00098 600/107 |
| 2018/0184887 A1* | 7/2018 | Abou El Kheir .... A61B 1/0008 |

FOREIGN PATENT DOCUMENTS

| | | |
|---|---|---|
| DE | 202013007316 U1 | 9/2013 |
| DE | 102012220578 A1 | 5/2014 |
| DE | 202013007416 U1 | 11/2014 |
| DE | 102013222279 A1 | 5/2015 |
| DE | 102013224683 A1 | 6/2015 |
| EP | 1132041 A2 | 9/2001 |
| JP | 10258022 A | 9/1998 |
| WO | WO-2015171113 A1 * | 11/2015 ......... A61B 1/00098 |

OTHER PUBLICATIONS

International Preliminary Report on Patentability for International Application No. PCT/EP2018/059265, dated Oct. 15, 2019, 8 pages.
International Search Report and Written Opinion for International Application No. PCT/EP2018/059265, dated Jun. 7, 2018, 10 pages.
European Communication pursuant to Article 94(3) with Search Report for European Application No. 18 717 590.6, dated Feb. 5, 2021, 7 pages.

* cited by examiner

ENDOSCOPE HEAD HAVING A PIVOTABLE CAMERA AND WORKING CHANNEL UNIT

CROSS REFERENCE TO RELATED APPLICATIONS

This application is the United States national phase entry of International Application No. PCT/EP2018/059265, filed Apr. 11, 2018, which claims the benefit of priority of German Application No. 10 2017 107 978.5, filed Apr. 12, 2017. The contents of International Application No. PCT/EP2018/059265 and German Application No. 10 2017 107 978.5 are incorporated by reference herein in their entireties.

FIELD

The present invention relates to an (endoscope-integral) endoscope head or an (endoscope-separate) endoscope-head attachment/endoscope head of the endoscope-adaptive type, respectively having at least one optical unit for image transfer, a lighting means, and a working channel for guiding (minimally invasive) tools and/or for through-flow of media. Furthermore, the invention relates to an endoscope with such an endoscope head or endoscope-head attachment.

BACKGROUND

Endoscopes are medical working tools used for the visual exploration of cavities in the body of a patient. They basically have optical devices at the distal endoscope end, i.e. the endoscope end facing the body (also known as endoscope head) and optionally a working channel which, starting from a proximal (not facing the body) endoscope portion or extracorporeal endoscope handle, extends through an (adjoining) flexible/bend-proof or rigid endoscope shaft to the endoscope head and enables the extracorporeal insertion and use of medical instruments such as forceps, scissors, needles, slings, knifes and the like.

Such endoscopes can optionally be provided with additional functions, e.g. by placing a cap or sleeve on the distal endoscope end/endoscope head radially on the outside of the endoscope head, which is provided or equipped with specific functions/functional elements, whereby the endoscope can not only be used for exploration and/or as access for therapeutic applications, but the endoscope itself can also be used as a minimally invasive instrument for performing a surgical procedure. Alternatively, it is provided to integrally equip special endoscopes for very specific medical applications with such functions, wherein such special designs are only suitable for this respective special application.

Various diagnostic and/or therapeutic procedures require, for example, imaging and/or, if necessary, therapeutic techniques on the biliary and/or pancreatic duct as well as on the hepatic ducts of the patient. Since the major duodenal papilla, which forms the common outlet of the biliary and pancreatic duct into the duodenum, protrudes laterally into the duodenum, conventional prograde endoscopes (facing in the longitudinal direction of the endoscope) are unsuitable for such procedures, since there is not enough pivoting space in the duodenum to orientate their prograde optical unit and the working channel in a lateral-facing position.

From the prior art (e.g. US 2010/228086 A), duodenoscopes are known which are specially made for this purpose, which have a lateral (lateral facing) or retrograde (backward facing) optical unit (also called "side optics") as well as a lateral-facing working channel. At the exit of the working channel of such duodenoscopes, a so called Albarrán lever is usually provided, which allows a targeted guidance/deflection of a tool guided in the working channel. The lateral-facing arrangement of the functional units on the endoscope head allows imaging and treatment in the duodenum area while optimally utilizing the available space.

However, such endoscopes with side optics are very complex and expensive to manufacture and have therefore been developed and manufactured so far as reusable devices. The curved working channel of such endoscopes as well as the complex construction with many undercuts of the Albarrán lever have proven to be non-sterilizable in practice or the sterilization process has turned out to be too material fatiguing for the filigree construction of the Albarrán lever, so that only disinfection is possible after surgery with such a duodenoscope. As a result, a bacterial lawn (biofilm) remains in the working channel and/or the auxiliary channel of the endoscope after a procedure. If this biofilm then peels off during a subsequent procedure, for example when an instrument is pushed through the working channel, it can, for example, enter the biliary duct and cause serious inflammation or even sepsis in the patient.

Furthermore, such devices have the disadvantage that they can only be used for very few, very specific procedures in the area of the duodenum, since neither the optical unit nor the working channel can be directed in the prograde direction. Moreover, navigation in the body with lateral-facing endoscopes is generally rather difficult, since looking ahead always requires bending of the "deflecting portion" (actively bendable endoscope shaft-portion) directly upstream of the endoscope head by about 90°, which in turn requires more space in the lateral direction of the endoscope, which is only available in the stomach. The printed publications DE 20 2013 007 416 U1, JP H10 258022 A, DE 10209986 A1, U.S. Pat. No. 5,413,107 A, and DE 10 2013224683 A1 disclose examples of prograde, flexible endoscopes with such a deflecting portion as described above. In some of the publications cited, the endoscope head is interchangeably attached to the distal deflecting portion end.

As described, for example, in the prior art in DE 10 2013 222 279 A1 or DE 10 2012 220 578 A1, endoscopes with a pivoting optical unit are furthermore known, which can look both in the prograde and in the lateral direction. However, such endoscopes do not have a working channel (i.e. they are used purely diagnostically) or they have a fixed working channel in the prograde direction and are therefore not suitable for the typically intended purposes of duodenoscopes which require a laterally-oriented working channel.

From the published patent application DE 10 2010 034 380 A1, an endoscope is known that has a pivot mechanism in the form of a four-joint gear, via which the distal tip of the endoscope can be connected to the proximal shaft.

In summary, the duodenoscopes known from the prior art so far are very expensive and costly to manufacture and are only suitable for a very specific intended purpose and also pose a considerable hygiene risk.

SUMMARY

In view of the disadvantages of the prior art described above, one target of the present invention is to provide or retrofit an endoscope which can/will be used both as a prograde endoscope and as a laterally-oriented endoscope. A further preferred target of the invention is to provide such an endoscope as a disposable article or to provide a corresponding retrofit kit, which can be used as a disposable product, in order to avoid the hygiene problems.

Basically, an endoscope head according to the invention (integral solution) or a (cap) attachment/endoscope head according to the invention of the endoscope-adaptive type (adaptive solution) which can be attached to the endoscope head of a conventional endoscope has at least one optical unit for image transfer, a lighting means, and a working channel for guiding tools and/or for through-flow of media. Moreover, the endoscope head/endoscope-head attachment according to the invention has an internal pivoting device which is different from the generally known "deflecting portion" (i.e. an additional pivoting device distally spaced therefrom) and which is designed to pivot, in particular continuously, if required, also steppedly, a portion of the endoscope head/endoscope-head attachment from a prograde orientation into a lateral or sideways orientation, i.e. about a pivot axis transverse to the longitudinal direction of the endoscope. At least the optical unit and the working channel are directly or indirectly coupled to the pivoting device, in such a way that they are pivoted together with the pivoting device or the endoscope head portion/attachment portion that can be pivoted by it. In other words, an endoscope head/endoscope-head attachment according to the invention forms a pivotable optical unit and working channel unit, so that an endoscope equipped/retrofitted with it can be used both prograde and laterally. The word "optical unit" in the context of this application summarizes all imaging devices known from the prior art in the field of endoscopy, such as a module made of CMOS or CCD chip and lens in the endoscope head/endoscope-head attachment or the use of light guides, etc. It is irrelevant whether the basic position of the pivoting device is prograde or lateral. In order to implement the inventive idea, it is only important that the pivoting device can adopt both orientations, so that an endoscope with an endoscope head/endoscope-head attachment according to the invention combines the functions of a prograde and an endoscope with side optics. As a pivoting device, basically any pivoting or rotating actuator/gear known to the prior art can be used. The pivotable mounting of the pivoting device can be designed, for example, as hinge with hinge pin and sleeves, as film hinge or as catch/edge that interacts with a corresponding guiding contour. For example, a Bowden cable can be used to trigger pivoting of the pivoting device, which can be operated proximally and outside of the patient. According to a preferred embodiment, the pivoting device can be prestressed in a defined position.

Preferably, in addition to the optical unit and the working channel, a so called auxiliary or secondary channel for additional suction and flushing and/or at least one lighting means for joint pivoting can be coupled with the pivoting device. In other words, with a preferred exemplary embodiment, all functional units usual in the prior art can be pivoted from a prograde orientation into a lateral orientation while maintaining their relative orientation to each other.

A pivoting device according to the invention for pivoting the optical unit and working channel offers numerous advantages over the endoscopes known in the prior art. One obvious advantage is that one single device can now be used flexibly for all tasks that previously required the purchase of several devices (gastroscope, colonoscope, duodenoscope). Compared to commercially available side-view endoscopes, an endoscope with an endoscope head/endoscope-head attachment according to the invention furthermore has the advantage that navigation in and to the duodenum is considerably simplified in the prograde position of the optical unit. I.e. where previously the endoscope tip had to be angled by 90° in order to be able to look straight ahead with a side-optical endoscope head, which is only possible within the stomach due to the small space available, the endoscope with endoscope head/endoscope-head attachment according to the invention can be inserted with a prograde viewing direction and is only pivoted into the lateral orientation at the site of use in a quite narrow space. A further advantage of an optical unit and working channel unit according to the invention is a significantly enlarged possible field of view.

The pivoting device can preferably be designed in such a way that the diameter or cross-sectional area of the endoscope head/endoscope-head attachment is increased as little as possible by pivoting. In concrete terms, this means that in contrast to the commercially available endoscope, which has to be angled via the deflecting portion, the cross-sectional area of the endoscope head/endoscope-head attachment does not or only slightly increases when it is transferred from the prograde to the lateral orientation or vice versa. In other words, the pivoting device may be designed to pivot in the head itself. According to an embodiment, the pivoting device can be designed in such a way that the cross-sectional area of the endoscope head does not increase by more than 25%, preferably by not more than 10%, especially preferably by not more than 5%, during pivoting. This functional feature can be implemented constructively, for example, by the fact that the extension of the endoscope head portion/attachment portion pivoted by the pivoting device is shorter in the longitudinal direction of the endoscope than its extension in the lateral direction of the endoscope.

Preferably, the optical unit of an endoscope according to the invention can allow a viewing angle (without consideration of pivoting movements) between 115° and 140°.

According to one aspect, the pivoting device can essentially be located (pivotably supported) on a peripheral edge of the endoscope head/endoscope-head attachment. In this way, for example, a complete distal portion of the endoscope/endoscope-head attachment can be pivoted together with all the functional units located on it or arranged on it.

In such an embodiment, the working channel formed in or on the endoscope head/endoscope-head attachment and/or the auxiliary channel may preferably be located on the side (diametrically) opposite the pivot axis. This has the advantage that a radius of curvature of the working channel that is as large as possible is achieved in the lateral position, so that kinking of the working channel can be avoided. According to an advantageous embodiment, the working channel can even be guided outside and along the endoscope head body/endoscope-head attachment and essentially (diametrically) opposite the pivot axis of the pivoting device, in order to increase the distance between the working channel and the pivot axis in order to avoid kinking of the channel.

According to a further embodiment, the working channel and/or the auxiliary channel can be per se designed to be resistant to kinking, e.g. by selecting a suitable material (e.g. PTFE) or by providing supporting tube layers such as wire spirals.

In a further advantageous exemplary embodiment, the endoscope head/endoscope-head attachment may have an (additional) kinking prevention device, which is designed to support the working channel which bends during pivoting of the pivoting device into the lateral orientation in order to prevent it even more effectively from kinking. This serves to ensure the passability of the working channel for surgical tools and media. Preferably, the kinking prevention device can be designed to fold out/extend into the lateral orientation when pivoting the pivoting device and to fold in/retract again when pivoting back. The folding and unfolding kinematics can be performed, for example, via a pair of guiding contours or a spring pre-load. Preferably, the kinking prevention device can support the working channel in its curved state by a desired shape.

According to a further aspect of the invention, the endoscope head/endoscope-head attachment may have a guiding device/sight which is designed to indicate the orientation of the pivoting device. It is advantageous if the orientation of the working channel opening is projected onto a lumen or other tissue to be examined. For this purpose, the sight may preferably have a light pointer or laser pointer, which is essentially orientated towards the distal exit of the working channel within the pivotable portion of the endoscope head/endoscope-head attachment. This has the advantage that during treatment, the user can see through the optical unit of the endoscope at which point a tool (medical instrument) guided, if applicable, through the angled working channel will abut or how far the user has to angle the pivoting device in order to intubate the major duodenal papilla.

According to a preferred embodiment, the endoscope head/endoscope-head attachment may furthermore have a tube or bellows structure connecting the pivoting device to the proximally adjacent non-pivoted portion of the endoscope head/endoscope-head attachment or shaft portion. If the pivoting device is now pivoted relative to the proximally adjacent portion of the endoscope head/endoscope-head attachment or shaft portion, a gap that normally occurs as a result of this pivoting movement is closed to the environment by the tube portion or bellows structure, which is preferably elastic in the longitudinal direction of the endoscope. In other words, the pivoting space of the pivoting device can be sealed by the tube or bellows structure. Such a bellows, which extends in the manner of an accordion when one portion of the endoscope head/endoscope-head attachment is pivoted, can at the same time assume the function of the above-mentioned kinking prevention device if the working channel is located radially outside the endoscope head/endoscope-head attachment and thus lies on the outside of the bellows.

According to a particular, preferred aspect of the invention, the endoscope head according to the invention can be designed as an adaptable endoscope head or endoscope-head adapter. This means that the endoscope can have a kind of connection mask on the distal front side of the "deflecting portion" to which the endoscope head can be coupled with the corresponding function as described above, or the endoscope-head adapter can be detachably attached to an endoscope-head surface, preferably a front surface, of an already known endoscope and thus serve as a retrofit attachment as described above. In other words, with the help of such an adapter, a commercially available endoscope head can be converted to an endoscope according to the invention with a pivoting device for pivoting the optical unit and the working channel. Such an endoscope-head adapter can adopt the already existing functional units of the endoscope to be retrofitted, i.e. it can be operatively connected/coupled to the optical unit and/or the lighting means and/or the working channel and it can be designed to forward at least the adapter-internal optical unit and the working channel over the axial length of the adapter and to pivot them accordingly with the help of the pivoting device. In the same way, the endoscope-head adapter can also have its own internal optical unit and/or lighting means and/or its own working channel (in addition to/parallel to the elements built into the endoscope head) guided along the retrofitted endoscope. In the same way, any combination is possible, i.e. that some functional units of the retrofitted endoscope are used while other functional units are formed independently of the retrofitted endoscope (in parallel thereto). The adaptability of such an endoscope head designed as an adapter can be implemented, for example, by paired threads, a latch or push-on mechanism, or adhering via vacuum. An endoscope-head adapter according to the invention may preferably be designed as a disposable article, whereas the endoscope can be a reusable article. This has the advantage that a conventional prograde endoscope may be equipped with the pivoting device according to the invention, while the hygiene-critical components (first of all the different channels) can be disposed of after use.

A further aspect of the invention, which may possibly be independently claimed, relates to an endoscope, in particular a disposable endoscope with an endoscope head/endoscope-head attachment according to the invention as described above.

In order to allow for treatment in the area of the duodenum, such an endoscope comprises, apart from an endoscope head/endoscope-head attachment according to the invention as described above, a preferably flexible shaft through which and/or along which various operating and supply channels extend, which enable a connection of the various functional units of the endoscope head with a proximal operating station as well as a control/handle. By an implementation of the endoscope according to the invention as a disposable article which can be attached to a reusable handle, the hygiene problem described above disappears, since all components inserted into the body are disposed of after the treatment.

Preferably, an endoscope according to the invention may have an actively-bendable distal shaft portion, a so called deflecting portion, which is designed to be actuated by the user via the control/handle from outside the patient and thus enable bending of the deflecting portion in at least one direction. The deflecting portion preferably borders proximally to the endoscope head. The deflecting portion may be all embodiments in the prior art, e.g., a configuration with Bowden cables and articulated vertebrae/links or a configuration with hydraulic actuators.

According to a further preferred embodiment, the endoscope according to the invention may comprise a rotary transmission or a rotating kinematics for rotating a distal portion of the endoscope or the endoscope head around its longitudinal axis. In other words, it is advantageous if at least the portion of the endoscope or the endoscope head in which the pivoting device is arranged, can be rotated around the longitudinal axis of the endoscope. In this way, the radius of effect of the pivotable optical working-channel unit can be significantly further increased. Preferably, the rotating gear can be arranged between the proximal end of an (actively-bendable) deflecting portion and the distal end of the flexible, passively-bendable shaft. Preferably, an endoscope according to the invention rotatable in this way can have a deflecting portion which can only be bent in one direction. In this way, the (rotatable) deflecting portion can be bent in practically any direction, while the deflecting portion can be produced in a simpler, less expensive, and slimmer manner.

BRIEF DESCRIPTION OF THE DRAWING FIGURES

The invention is described in the following based on preferred exemplary embodiments with reference to the associated figures.

DETAILED DESCRIPTION

Figure 1:
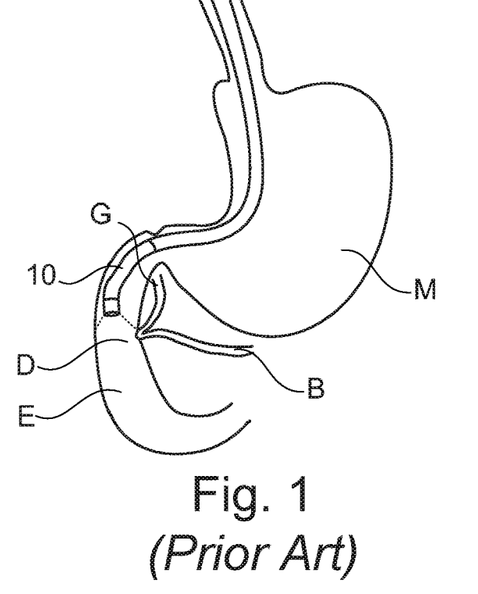
FIG. 1 is a schematic of a prograde endoscope according to the prior art during the exploration of a duodenum.
Figure 2:
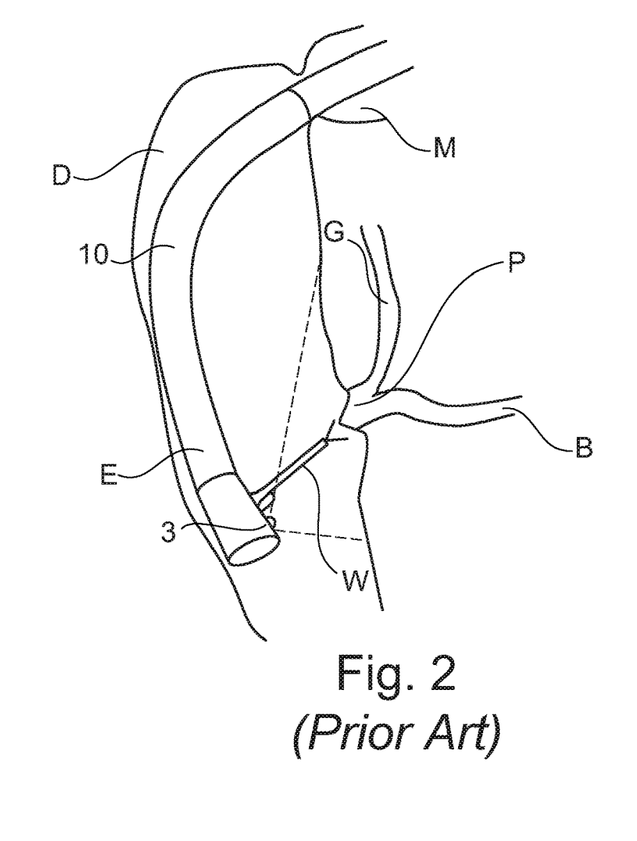
FIG. 2 shows a detailed view of a duodenoscope known from the prior art during a procedure at the major duodenal papilla.

FIGS. 1 and 2 are used to explain a preferred field of application of an endoscope according to the invention or an endoscope head according to the invention as well as the endoscopes known from the prior art for this purpose so far.

As can be seen from FIG. 1, the major duodenal papilla (P) (the entrance of the biliary duct (G) and the pancreatic duct (B) into the duodenum) is located in the rearward (dorsal) descending part (Pars descendens) of the duodenum (D) and relatively difficult to access due to the tortuous geometry of this system. The space available in the region of the duodenum (D) is very limited, which means that procedures on the major duodenal papilla (P) are not possible with prograde endoscopes, since at an appropriate angle the endoscope tip or deflecting portion 10 would no longer have sufficient distance to the lumen of the duodenum (D) for proper imaging in the direction of the procedure portion. Bending the deflecting portion 10 in the duodenum (D) also poses the risk of injury due to the confined space. In the worst case, the lumen of the duodenum could tear during such a maneuver.

Due to this reason, the above mentioned duodenoscopes (E), which have a lateral-facing optical unit as well as a correspondingly orientated working channel, are known to the prior art in order to make optimal use of the available space (cf. FIG. 2). Since such an optical unit has a viewing angle of 125° to 140°, the endoscope can also be used retrospectively/retrogradably. However, such duodenoscopes (E) have the disadvantage that they are fixed in their lateral orientation of the optical unit and the working channel. On the one hand, this makes general navigation within the patient more difficult and on the other hand makes such endoscopes inflexible in their application possibilities. Moreover, such duodenoscopes are not sterilizable so far, but can only be disinfected, which makes them a considerable hygiene risk.

A basic idea of the present invention is therefore to provide an endoscope, in particular an endoscope head or an endoscope-head attachment, in which the internal optical unit and working channel are designed to be pivotable together by at least 90° (without the deflecting portion having to be actively pivoted) in order to enable operation both in prograde orientation and in lateral orientation. In other words, the main purpose of this invention is to provide a combination device that combines the functions and advantages of a prograde gastroscope or colonoscope with those of a duodenoscope in one device.

Figure 3:
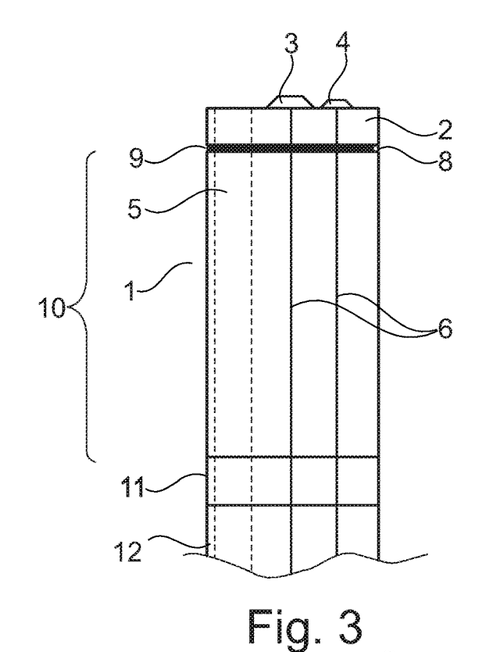
FIG. 3 shows a representation of a first exemplary embodiment for an endoscope according to the invention in an unbent, prograde orientation.

FIG. 3 shows a first exemplary embodiment of an endoscope 1 according to the invention in a first prograde orientation. The endoscope 1 has an endoscope head 2 at its distal end, which has different functional units such as an optical unit 3, a lighting means 4, and a working channel 5. For the sake of clarity, only the most necessary functional units mentioned above are shown here and in the following; of course, an endoscope head according to the invention can also have various other functional units known from the prior art, such as cleaning nozzles for a lens of the optical unit 3, etc.

The working channel 5 extends from its distal opening or its exit at the distal front side of the endoscope head 2, through a flexible shaft or along a flexible shaft of an endoscope 1 equipped with the endoscope head 2, to a proximal opening in the area of the endoscope handle and can thus be used, for example, for the introduction of surgical instruments or tools (W), such as a papillotome, or for the application of media in the patient. The shown endoscope 1 furthermore has functional and supply channels 6, such as electrical lines, for supplying the functional units, for transmitting data, and for controlling the movements of the endoscope, which can be connected in the proximal direction to an operating station (not shown) or a controller/control device (also not shown). Furthermore, such an endoscope of the shaft type can have a so called deflecting portion between the endoscope head and the preferably flexible endoscope shaft, which represents an actively-bendable shaft portion in extension of the passively-bendable endoscope shaft. This actively-bendable shaft portion can either be bendable in all directions or, if applicable, only in one direction, whereby in the latter case a rotation ring can be arranged between the deflecting portion and the endoscope shaft, which keeps the deflecting portion rotatable around the longitudinal axis of the endoscope with respect to the endoscope shaft.

Figure 4:
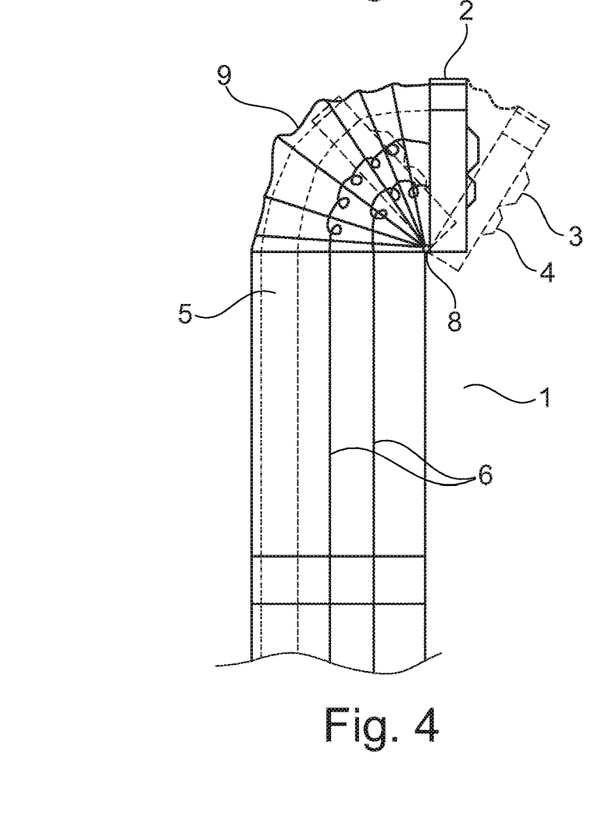
FIG. 4 shows a representation of the first exemplary embodiment for an endoscope according to the invention in a bent, lateral or sideway facing orientation.

In order to allow the transfer of the endoscope head 2 or a preferably distal head portion from a prograde orientation to a lateral-facing orientation, the endoscope or the endoscope head has a pivoting device 7. In the first exemplary embodiment, this is implemented as a combination of a hinge 8 and a Bowden cable (not shown) and allows in the example shown pivoting of the entire endoscope head 2 preferably by an angle>90°, so that the front surface of the endoscope head 2 is laterally orientated after pivoting. The hinge 8 can, for example, be realized by a bolt guided in sleeves, a film hinge, or a catch guided in a corresponding groove/guiding contour.

Since such a pivoting process results in an opening or gap between the pivoted head 2 and the shaft portion proximally adjacent to it, a bellows, for example, is provided as sealing element 9 to maintain the sterile barrier in the area of the pivoting space, the bellows being expandable/stretchable in the longitudinal direction of the endoscope, in particular on the side facing away from the hinge. Instead of a bellows, an elastic, tubular connecting element can also be used. It is only important that the sealing element 9 forms a sealed lumen together with the head and shaft and can be reversibly expanded/stretched in the longitudinal direction to bridge the distance covered by pivoting. Also for the purpose of reversible extensibility, the functional and supply channels 6 shown in the first preferred exemplary embodiment are spirally wound. The working channel 5 is also preferably designed as a bellows or elastic tube in the pivoting range.

A bendable shaft portion 10, the so called deflecting portion, borders proximally on the sealing element 9 in the exemplary embodiment shown above, as already indicated above. This can, for example, as is usual in the prior art, have a large number of links/vertebrae connected in series and pivotable together, which can be bent in one or more directions with the aid of Bowden cables or hydraulic actuators. In particular, such a deflecting portion 10 can achieve a degree of curvature of at least 180° in one direction.

A rotary transmission 11 borders proximally to the deflecting portion in the first preferred embodiment and is thus connected between the deflecting portion 10 and the passively flexible endoscope shaft 12. The rotary transmission 11 is designed to allow relative rotation between the shaft portions 10, 12 proximally and distally adjacent to the same. This has the advantage that in order to orientate the endoscope head 2, in particular in the pivoted state, not the entire endoscope 1 has to be rotated, which would result in considerable inconvenience for the patient. Instead, a distal portion of the endoscope can be rotated to a desired orientation in a targeted manner. The rotary transmission could also be directly proximally adjacent to the endoscope head 2. The rotary transmission 11 can be implemented by means of various gears or rotary feedthroughs known from the prior art for the concentric relative rotation of two components. Typical examples are ring mounts, planetary gears or electro-hydraulic slip ring systems.

Figure 5:
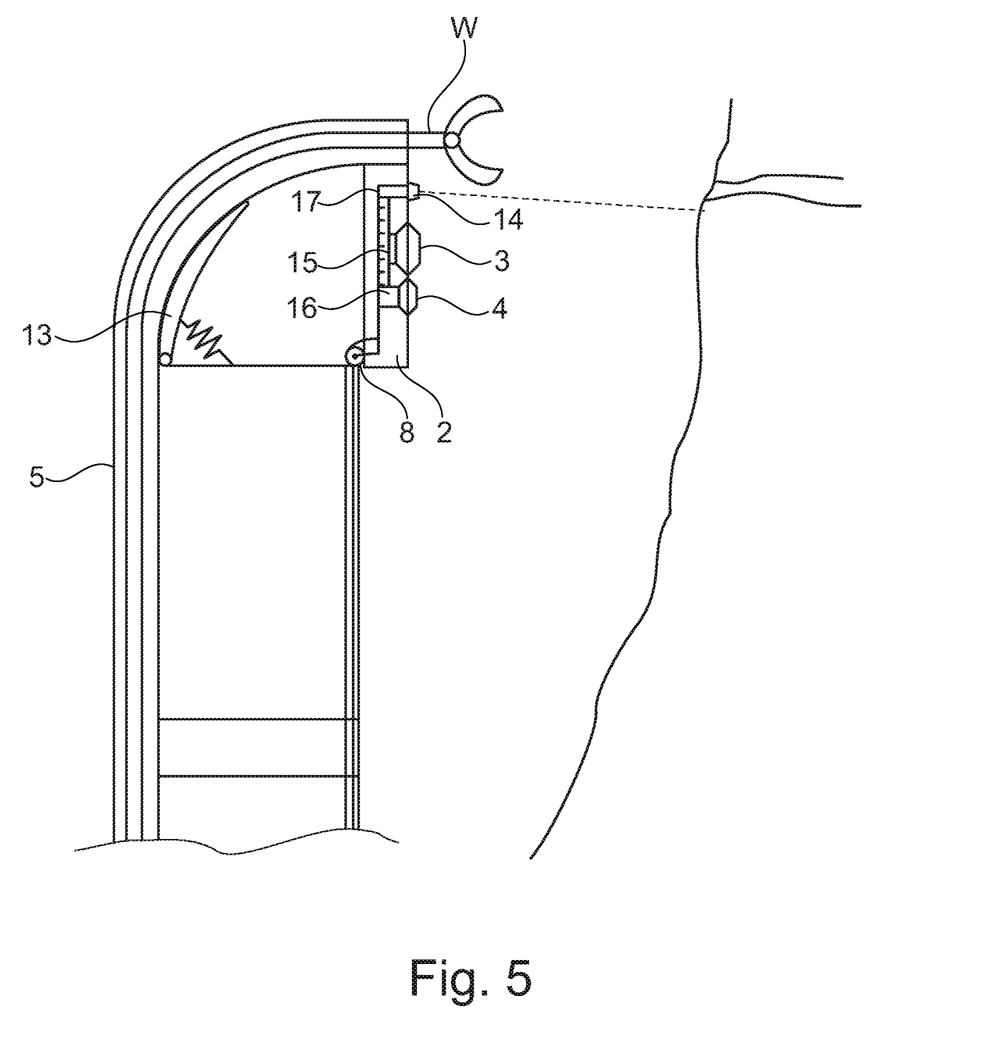
FIG. 5 shows a representation of a second exemplary embodiment for an endoscope according to the invention in a bent, lateral or sideway facing orientation.

FIG. 5 shows an endoscope with an endoscope head according to a second, preferred exemplary embodiment. As shown here as an example, the working channel 5 can also be guided externally on the endoscope shaft and head, preferably on the side diametrically opposite or facing away from the hinge 8, in order to maximize the bending radius of the working channel 5 in the lateral/sideways orientation. An additional feature of this configuration is an optional kinking prevention device 13 or a support element, which defines a shape contour along which the working channel 5 bends. In this way, it is possible to prevent the working channel 5 from kinking and the consequent blocking of the passage for medical instruments/tools. The kinking prevention device 13 is preferably designed to fold into the lateral orientation when the pivoting device 7 is pivoted, e.g. by a spring pre-load, and to fold back again when the pivoting device 7 is pivoted back, e.g. by a guiding contour. Alternatively, the bellows can also be used as described above to radially support the working channel outside the bellows and thus avoid kinking.

In the second embodiment shown, the sealing element 9 is designed as an elastic silicone tube. In this exemplary embodiment, the electrical functional and supply channels are guided into the endoscope head in the edge area of the shaft and over the hinge 8, in order to supply the lighting means 4 designed as LEDs 16 and an image sensor 15 of the optical unit 3 designed as a CMOS chip arranged on a circuit board 17. In the endoscope head 2 or on the circuit board 17 in the exemplary embodiment shown, a light pointer 14 or a laser sight is also arranged, which is essentially arranged parallel to the distal exit of the working channel 5, in order to mark/indicate the approximate point of impact of a tool guided through the working channel at a target point in the patient by a light spot.

In the example shown, the optical unit 3 is a CMOS chip 15 that cooperates with a lens system. Other solutions known in the prior art are also conceivable. For example, the image sensor 15 can also be shifted in the proximal direction and the image can be guided to it by light guides (prisms and/or glass fibers). The one or more lighting means 4 can also be shifted in the proximal direction.

Figure 6:
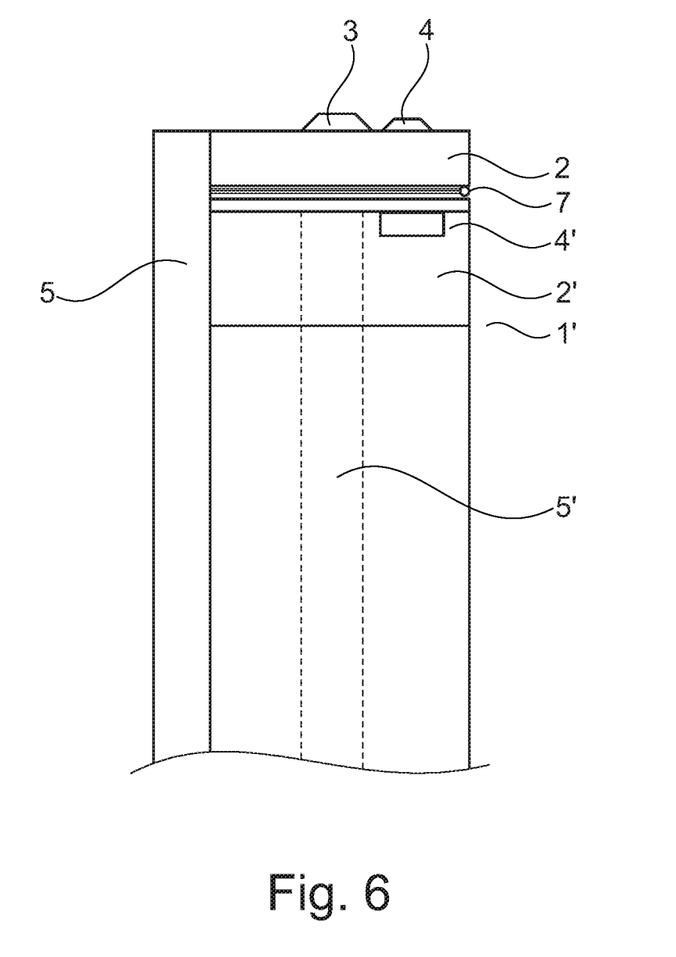
FIG. 6 shows an endoscope-head adapter according to a preferred embodiment of the invention.

FIG. 6 shows a further embodiment of the present invention, which may possibly be claimed independently. In this case, the endoscope head 2 shown is designed as a separate adapter (endoscope-head attachment) which can be detachably attached to a commercially available endoscope 1' or its internal endoscope head 2'. The centrally arranged working channel 5' of the retrofitted endoscope 1' can furthermore be used to apply a negative pressure to an appropriately prepared portion of the underside of the endoscope-head adapter 2 and thus to fix the endoscope-head adapter 2 to the endoscope 1'. The optical unit 3 of the endoscope-head adapter 2 shown here is independent of the internal optical unit of the endoscope 1' that is not shown here. Furthermore, the shown endoscope-head adapter 2 has its own working channel 5 for guiding tools as well as its own auxiliary channel, which are arranged along the endoscope (externally) and which are designed to pivot together with the pivoting device 7. Furthermore, the endoscope-head adapter 2 shown has its own lighting means 4. The autarkic endoscope-head adapter 2 formed in this way is furthermore connected or connectable to its own control device (separate from that of the endoscope 1') for controlling the pivoting device as well as to its own power supply connections and pump connections.

It is decisive for all exemplary embodiments mentioned above, i.e. for the integral or adaptive solution, that the working channel as well as the optical unit currently in charge of imaging are simultaneously pivoted by the same angle, so that the optical unit and the distal opening of the working channel are always orientated in the same coordinated direction. This ensures that the endoscope can be optimally used for different purposes. In particular, when the adaptive solution concept is implemented in practice, the additional advantage is achieved that commercially available endoscopes can be used, whereby the hygiene problem can be solved elegantly by providing the adaptive endoscope-head attachment with a pivotable attachment portion with an additional/separate optical unit and additional/separate working channel as a disposable product.

The invention relates in summary to a:

An endoscope head (2) of the endoscope-integral type at the distal end of a deflecting portion (10) of an endoscope having at least     an optical unit (3) of its own for image transfer;
    a lighting means (4) or light guide of its own; and
    a working channel (5) of its own for the guidance of medical tools (W) and/or for through-flow of media The endoscope head (2) has an additional pivoting device (7) distally spaced from the deflecting portion (10), which is designed to pivot, in particular continuously, at least a portion of the endoscope head (2) from a prograde orientation into a lateral or a retrograde orientation and at least the optical unit (3) and the working channel (5) are directly or indirectly coupled to the pivoting device (7) such that they are pivotable together with the at least one portion of the endoscope head while maintaining their relative orientation to each other.

As well as an endoscope head of the endoscope-adaptive type in the manner of a separate, additional endoscope-head attachment which has a fastening means for detachable attachment to the endoscope head of an endoscope, having at least     an optical unit (3) of its own for image transfer;
    a lighting means (4) or light guide of its own; and
    a working channel (5) of its own for the guidance of medical tools (W) and/or the through-flow of media. The endoscope head (2) of the adaptive, attachment-like design has an internal pivoting device (7) which, in the fixed state, is designed to pivot, in particular continuously, at least a portion of the endoscope head (2) from a prograde orientation into a lateral or a retrograde orientation and at least the optical unit (3)

and the working channel (5) are directly or indirectly coupled to the pivoting device (7) such that they are pivotable together with the at least one portion of the endoscope head while maintaining their relative orientation to each other.

The invention claimed is:

1. An endoscope comprising:
a flexible endoscope shaft;
a manually bendable deflecting portion connected to a distal end of the flexible endoscope shaft;
an endoscope head connected to a distal end of the manually actively-bendable deflecting portion and having a distal end with a working channel outlet opening, an optical unit and a light source;
a working channel extending along the endoscope shaft, the deflecting portion and the endoscope head, and terminating at the working channel outlet opening at a distal end of the endoscope head;
a pivot mechanism connecting the endoscope head to the distal end of the manually bendable deflecting portion, wherein the pivot mechanism is manually actuatable independently from the manually bendable deflecting portion, and wherein the pivot mechanism comprises a hinge configured to allow the endoscope head to pivot between an unbent orientation in which the working channel outlet opening, optical unit, and light source are oriented along a longitudinal axis of the distal end of the manually bendable deflecting portion, and a bent orientation in which the working channel outlet opening, optical unit and light source are oriented sideways relative to the longitudinal axis of the distal end of the manually bendable deflecting portion; and
a support element which is a member separate from the endoscope head and has at least one contour surface, wherein the support element as well as any element fixedly and non-movably connected to the support element or formed integrally with the support element is free of driving cables fixed directly to the support element as well as any element fixedly and non-movably connected to the support element or formed integrally with the support element;
wherein, when the endoscope head is held in the bent orientation via the pivot mechanism, the support element is biased by a spring such that the at least one contour surface is biased into contact with the working channel by a restoring spring force of the spring to hold the working channel with a predetermined curvature contour defined by the at least one contour surface.

2. The endoscope according to claim 1, wherein the working channel is arranged in or on the endoscope head on a side of the endoscope cross-section opposite the pivot axis of the pivoting device.

3. The endoscope according to claim 1, wherein electrical functional and supply channels of the optical unit and of the light source are guided from the manually bendable deflecting portion into the endoscope head.

4. The endoscope according to claim 1, further comprising a guiding device configured to indicate an orientation of the pivot mechanism and/or of the working channel outlet opening at the distal end of the endoscope head.

5. The endoscope according to claim 1, further comprising a sealing element connected between the manually bendable deflecting portion and the endoscope head, the sealing element being expandable away from the manually bending deflecting portion when the endoscope head is moved to the bent orientation, and wherein the sealing element is configured to form a sealed passage between the manually bendable deflecting portion and the endoscope head.

6. The endoscope according to claim 5, wherein the sealing element has a tubular or bellows-like shape.

7. The endoscope according to claim 1, wherein said endoscope head is designed to be detachably fastened as an endoscope head adapter to the endoscope head surface or the endoscope shaft of the endoscope and to be operatively coupled to an endoscope-internal optical unit and/or an endoscope-internal lighting means and/or an endoscope-internal working channel of said endoscope.

8. The endoscope according to claim 1, wherein the support element is configured to fold open such that one end of the support element moves distally away from the distal end of the manually bendable deflecting portion upon movement of the endoscope head from the unbent orientation to the bent orientation, and to fold closed such that the one end of the support element moves proximally towards the distal end of the manually bending deflecting portion upon movement of the endoscope head from the bent orientation to the unbent orientation.

9. The endoscope according to claim 1, wherein:
the support element is pivotally connected to the distal end of the manually bendable deflecting portion at a location spaced from the hinge, the support element being pivotable around an axis transverse to the longitudinal axis of the distal end of the deflecting portion, and
upon movement of the endoscope head towards the bent orientation, the endoscope head is oriented to a first lateral side of the endoscope with respect to the longitudinal axis of the distal end of the deflecting portion, and the support element is configured to pivot to a second lateral orientation at a second lateral side of the endoscope, which is diametrically opposite to the first lateral side of the endoscope.

10. The endoscope according to claim 1, further comprising:
a control cable comprising a pulling cable having a distal cable portion connected to the endoscope head and configured to move the endoscope head between the bent orientation and the unbent orientation independently from a deflection control of the manually bendable deflecting portion, and wherein
the optical unit and the working channel are coupled directly or indirectly to the endoscope head such that they are movable while maintaining a fixed relative orientation of the optical unit and the working channel with respect to each other.

11. The endoscope according to claim 10, comprising a rotary transmission for rotating a distal portion of the endoscope or of the endoscope head about its longitudinal axis.

12. The endoscope according to claim 10, wherein the working channel is arranged on a lateral side of the endoscope head which is opposite to a direction of the lateral orientation of the endoscope head when the endoscope head is in the bent orientation.

13. The endoscope according to claim 10, wherein the control cable is exactly one single control cable.

14. The endoscope according to claim 10, wherein the hinge defines a pivot axis arranged substantially in an edge region on one side of a cross-sectional area of the endoscope head, with the pivot axis extending essentially tangentially with respect to an edge of the endoscope in said edge region.

15. The endoscope according to claim 1, wherein
the support element is arranged between the endoscope head and the deflecting portion and is pivotably connected to the deflecting portion such that it is pivotable into a lateral orientation where a working channel supporting surface of the support element is angled diagonally with respect to a longitudinal axis of the distal end of the deflecting portion, and
when the endoscope head is held in the bent orientation via the pivot mechanism, the working channel supporting surface of the support element is biased by the restoring spring force to contact the working channel and to support the working channel with the predetermined curvature contour.

16. The endoscope according to claim 1, wherein the flexible endoscope shaft is a passive, non-actively-driven shaft, and the bendable deflecting portion is actively driven.

17. The endoscope according to claim 1, further comprising:
a control cable for controlling the pivot mechanism by pulling on the control cable, the control cable having a distal cable portion connected to the endoscope head and configured to move the endoscope head between the bent orientation and the unbent orientation independently from a deflection control of the manually bendable deflecting portion.

18. The endoscope according to claim 17, wherein, when the endoscope head is in the bent orientation, the working channel comprises a flexible section extending between the distal end of the manually bendable portion and the endoscope head, and the support element is configured to generate the restoring spring force on the flexible section.

19. The endoscope according to claim 17, wherein the support element is passively biased by the restoring spring force to hold the working channel with the predetermined curvature contour independently of an operation of the pivot mechanism to move the endoscope head from the unbent orientation to the bent orientation.

20. The endoscope according to claim 1,
wherein, when the endoscope head is held in the bent orientation via the pivot mechanism, the support element is biased by the restoring spring force acting on the support element in a direction transverse to the longitudinal axis of the distal end of the deflecting portion to hold the working channel with a predetermined curvature contour defined by the at least one contour surface.

* * * * *